United States Patent [19]
Smocer

[11] Patent Number: 5,484,421
[45] Date of Patent: Jan. 16, 1996

[54] SAFETY SYRINGE

[76] Inventor: Anthony V. Smocer, 309 Dogwood Dr., Cross Junction, Va. 22625

[21] Appl. No.: 269,985

[22] Filed: Jul. 1, 1994

Related U.S. Application Data

[63] Continuation-in-part of Ser. No. 112,927, Aug. 30, 1993, abandoned.

[51] Int. Cl.$^6$ .............................. A61M 5/32; A61M 5/00
[52] U.S. Cl. ........................ 604/195; 128/919; 604/110
[58] Field of Search ................................... 604/110, 194, 604/195; 128/763–765, 919

[56] References Cited

U.S. PATENT DOCUMENTS

| | | | |
|---|---|---|---|
| 2,888,923 | 6/1959 | Da Cunha Reis | 604/194 |
| 4,904,242 | 2/1990 | Kulli . | |
| 4,974,603 | 12/1990 | Jacobs . | |
| 5,069,225 | 12/1991 | Okamura . | |
| 5,125,898 | 6/1992 | Kaufold, Jr. et al. . | |
| 5,211,628 | 5/1993 | Marshall . | |
| 5,211,629 | 5/1993 | Pressly et al. . | |
| 5,279,580 | 1/1994 | Wallingford | 604/195 |
| 5,338,311 | 8/1994 | Mahurkar | 604/195 |

*Primary Examiner*—C. Fred Rosenbaum
*Assistant Examiner*—Frank Wilkens, III
*Attorney, Agent, or Firm*—McDermott, Will & Emery

[57] ABSTRACT

A blood sampling aspirator used to withdraw blood into vials for subsequent tests presents a hazard to personnel when withdrawing the hypodermic syringe because of the exposed needle. This invention encompasses an integral syringe design that allows for removal of the needle from the syringe even before the needle is withdrawn from the site of the needle puncture. The needle is contained within a ballistic type component which is withdrawn from the puncture site and from the syringe through the action of component elastic deflections and a force toggle mechanism without the use of coil spring devices. The needle is forcibly propelled into a tubular storage container toward the back of the syringe (toward the syringe operator and away from the patient). After the needle is propelled into the container it offers full protection from inadvertent needle punctures or scratches. The syringe, less the needle, can, if desired, be reused and another needle installed inside the syringe.

7 Claims, 10 Drawing Sheets

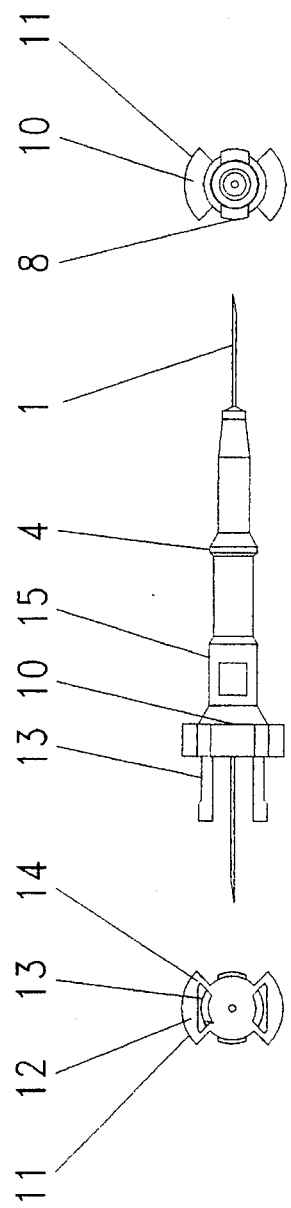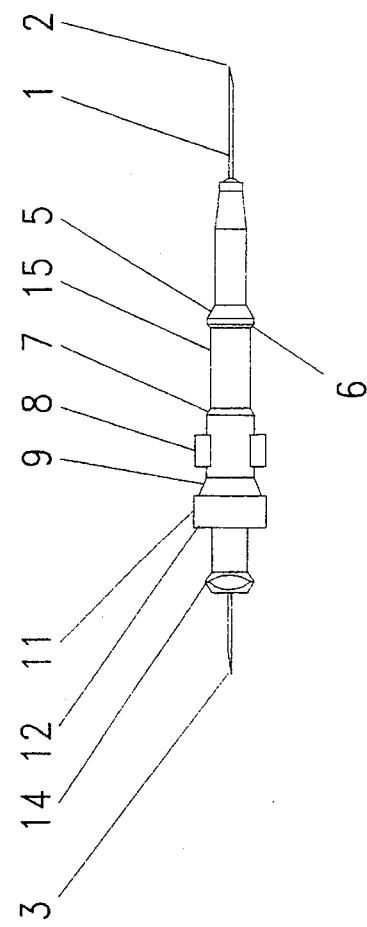
FIG. 3A  FIG. 3B  FIG. 3C  FIG. 3D

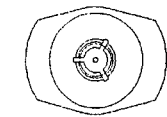
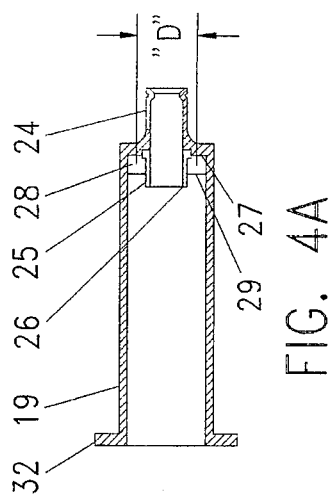
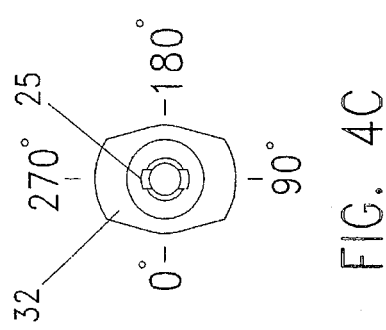
FIG. 4E
FIG. 4A
FIG. 4C
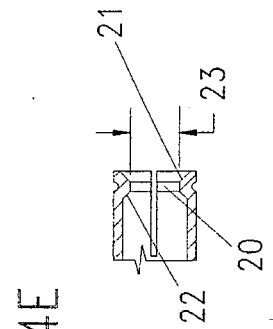
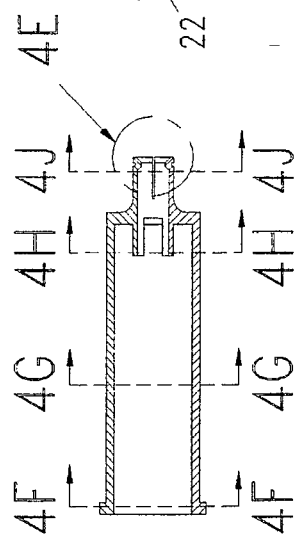
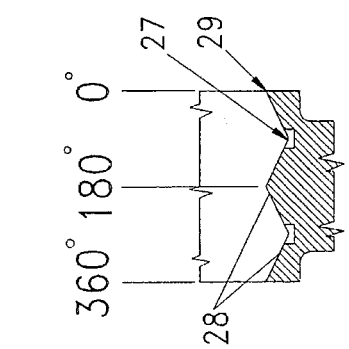
FIG. 4D
FIG. 4B
FIG. 4K
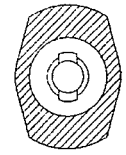
FIG. 4J
FIG. 4H
FIG. 4G
FIG. 4F

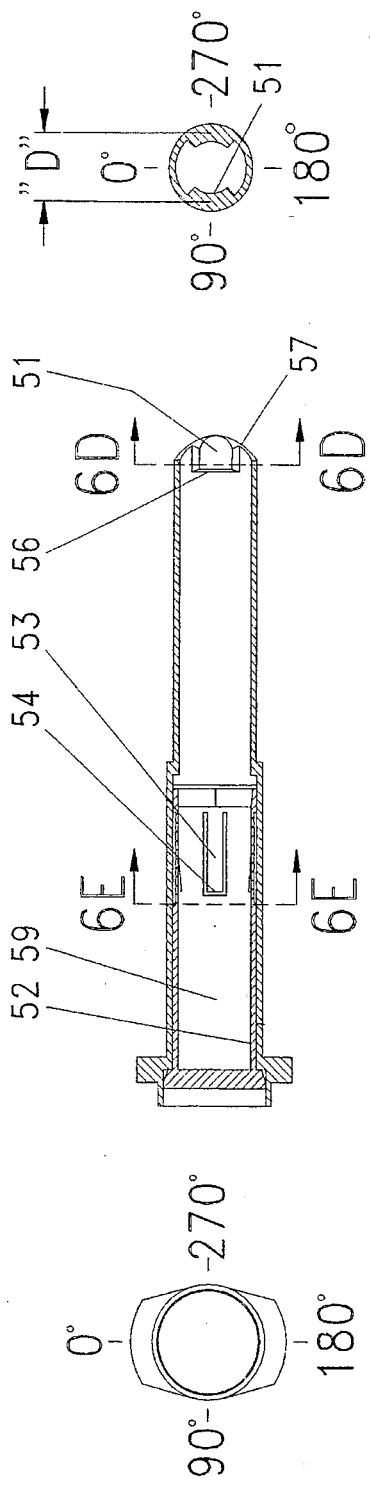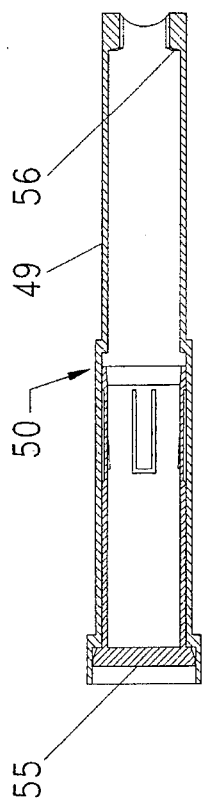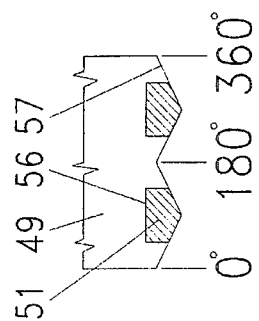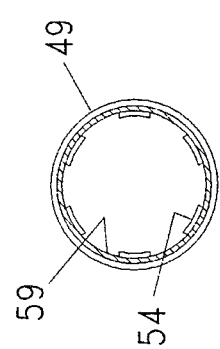

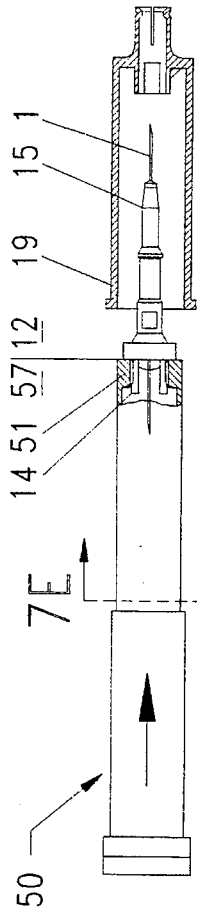
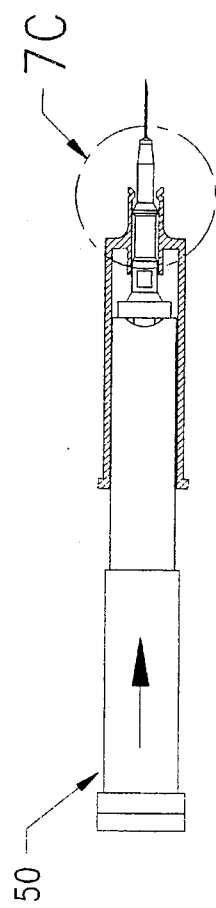
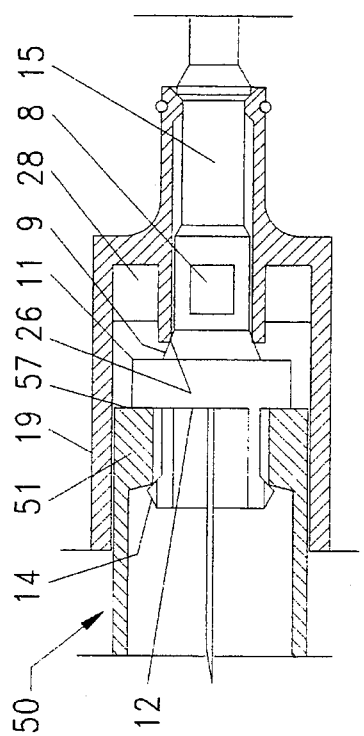
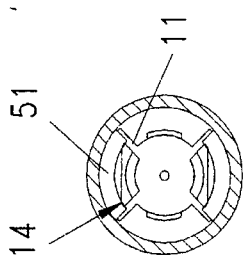
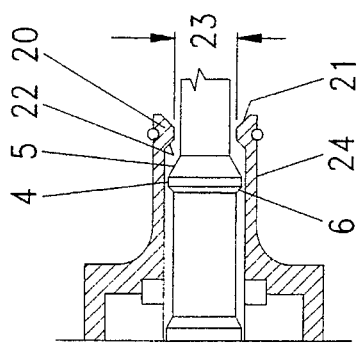

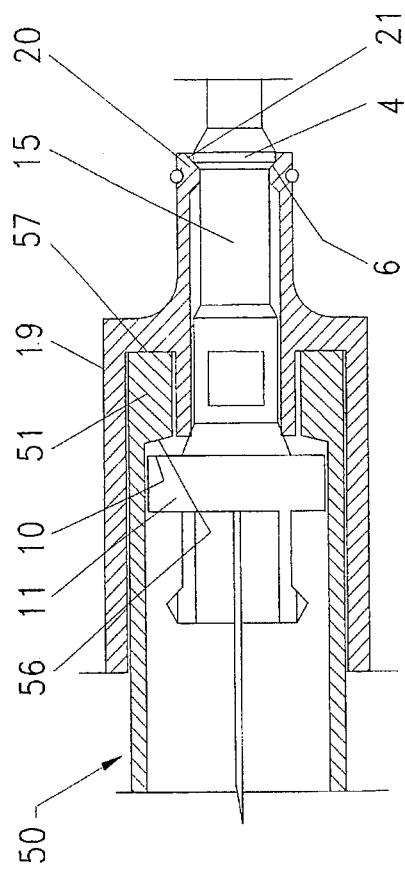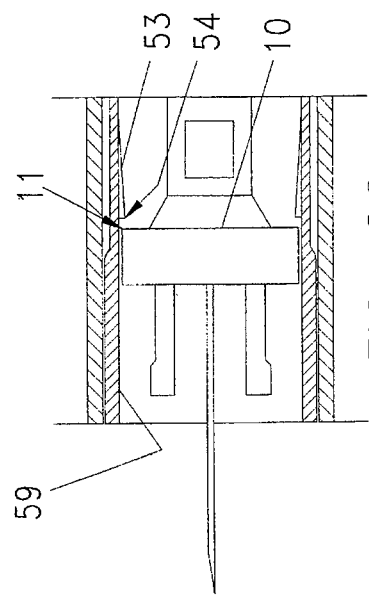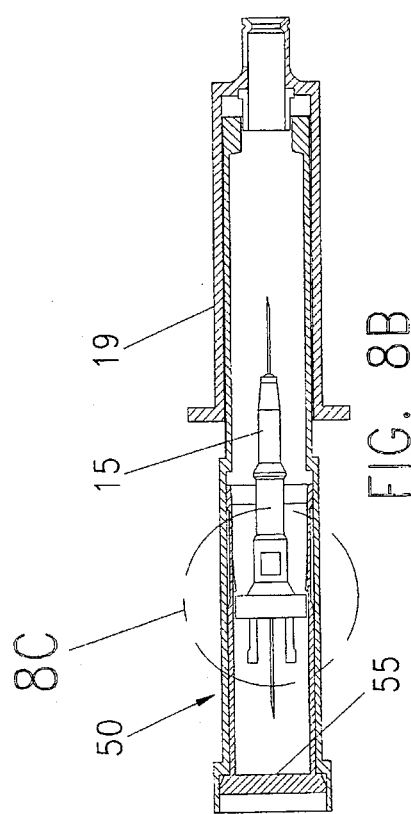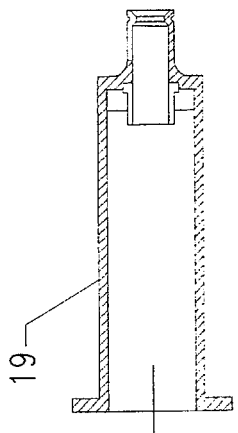

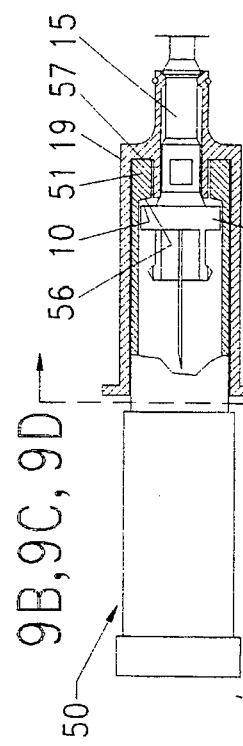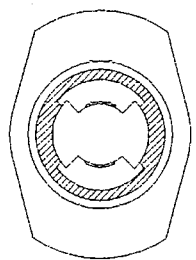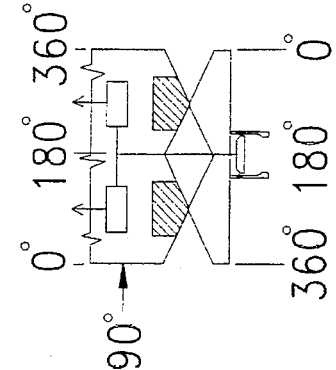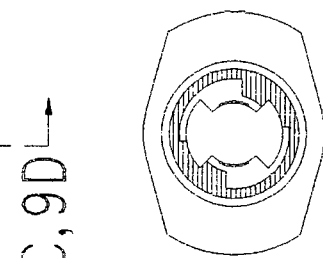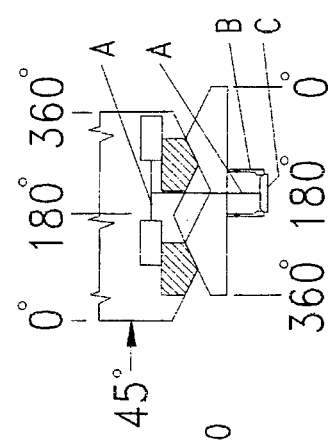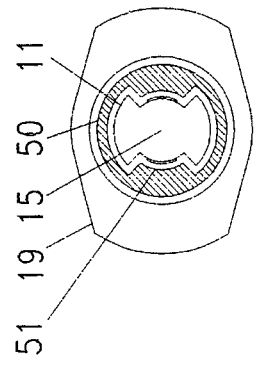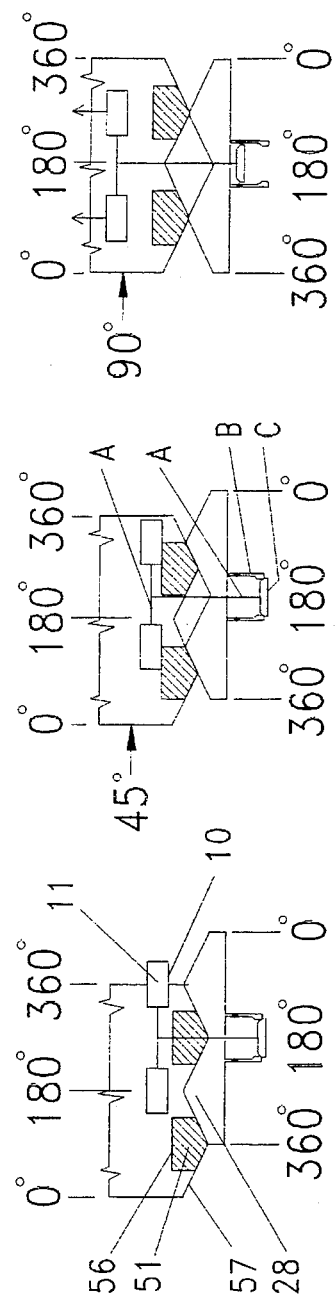

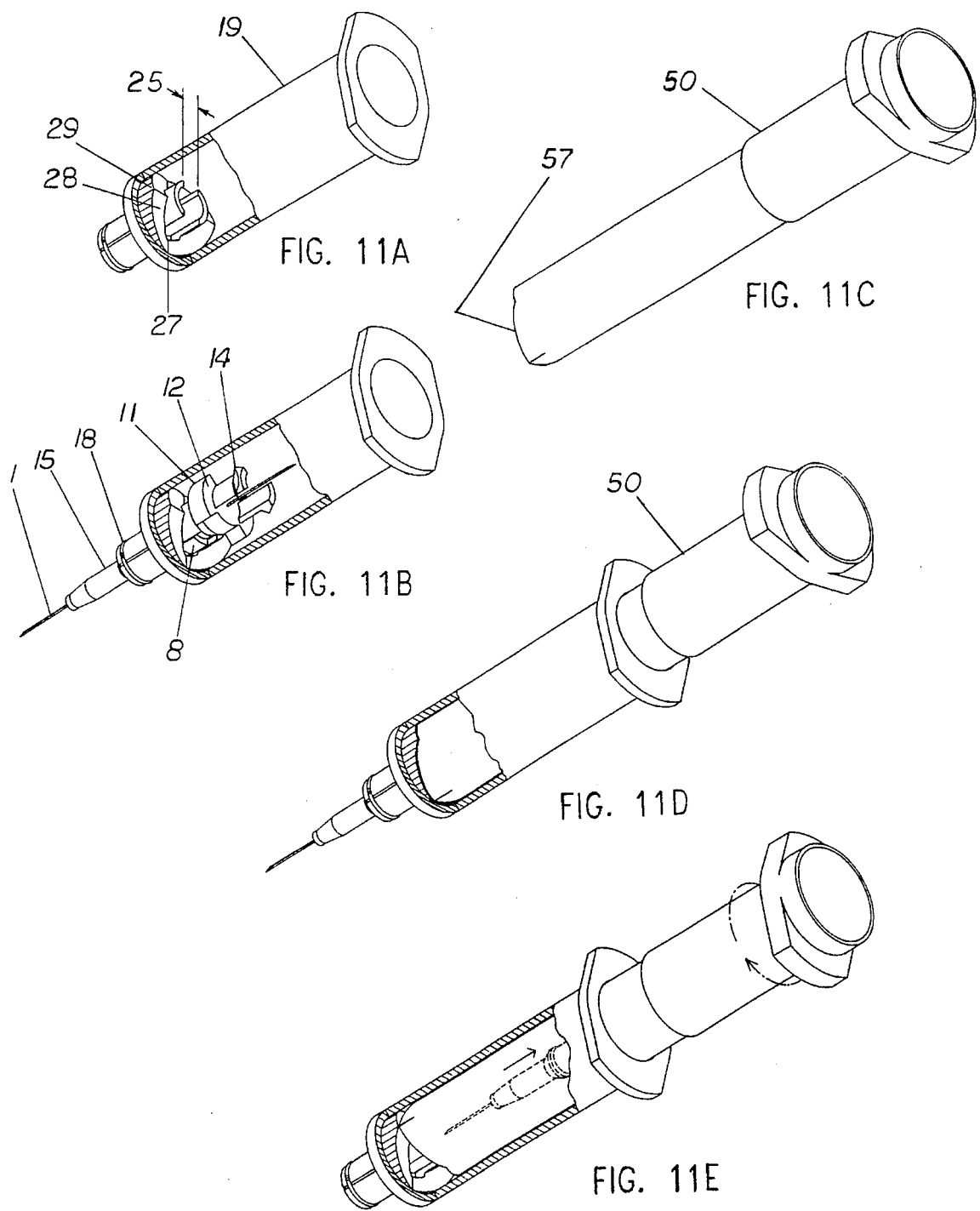

SAFETY SYRINGE

CROSS-REFERENCE TO RELATED APPLICATION

This application is a continuation-in-part of prior U.S. application Ser. No. 08/112,927 filed Aug. 30, 1993, abandoned.

BACKGROUND OF THE INVENTION

1. Field of The Invention

This invention generally relates to a hypodermic syringe and needle assembly of the type capable of encapsulating the exposed needle for the safety of health care personnel and patients.

2. Description of Related Art

Because of the potential danger to medical and health care workers and others caused by contact with or puncture from a used hypodermic needle, many proposals have been suggested to reduce or eliminate this danger.

Previously, some disposable hypodermic syringes have been manufactured with a protective detachable cover over the needle which can be too easily removed or lost, for example, should the syringe be dropped or knocked against some object.

Protective sleeves for hypodermic needles have been previously suggested in U.S. Pat. Nos. 3,040,743 to Naess; 3,314,428 to Johnson et al.; 4,695,274 to Fox; 4,655,751 to Harbaugh and 4,772,272 to McFarland.

The above prior art syringes include a protective sleeve which is fitted over the needle. The protective sleeve is slid away from the needle to accomplish the injection. The syringes are intended to be disposable, that is, intended for one-time use only.

More recent related syringe disclosures have been disclosed in U.S. Pat. Nos. 5,125,898 to Kaufhold, Jr. et al.; 5,211,629 to Pressly, et al.; 5,211,628 to Marshall; 5,069,225 to Okamura; 4,974,063 to Jacobs; and 4,904,242 to Kulli. Except for Okamura and Jacobs, the remaining four patents use passive means, that is, coil spring energy or differential pressure, to expel the needle from the syringe into a tubular depository inserted within the syringe. Okamura and Jacobs provide for release of the needle without providing for direct capture of the needle.

Kaufhold, Jr. et al., U.S. Pat. No. 5,125,898, discloses a disposable hypodermic syringe for injecting fluid into a patient. Axial force is applied to an air evacuated plunger tube, which acts as a needle storage container, that ruptures two sacrificial components, one which releases the needle from the syringe body, and the other that separates a pressure seal member at the bottom of the plunger tube. When these actions are performed, the pressure seal component attaches to the needle assembly and is pushed into the plunger tube by ambient air pressure.

As in Kaufhold, Pressly, et al., U.S. Pat. No. 5,211,629, describes a hypodermic syringe for injecting fluid which, with applied force by a containment tube, ruptures sacrificial components to free the needle and also to pierce an opening through the closed end of the plunger tube for needle passage and containment. The energy to expel the needle into the containment tube is supplied by a previously installed and charged coil spring.

Marshall, U.S. Pat. No. 5,211,628, also incorporates a coil spring to provide the energy to withdraw a needle into containment within a closed tube which acts also as the plunger to inject fluid. The spring is maintained compressed between the closed top end of the tube and another tapered component press fitted into the lower end. When axial force is applied, the tube lower end deflects outward a needle holding collar to free the needle. At a predetermined axial motion, the tapered fit holding the spring force is released allowing the spring to push the needle into containment.

Kulli, U.S. Pat. No. 4,904,242, describes a needle removal, spring expelling and containment design similar in action to Marshall. In addition, except for the sacrificial components used by Pressly, et al. it appears that the three disclosures are similar, providing like actions and require coil spring energy to expel the needle. In addition, these designs all require high axial forces to rupture and/or release the hold on the needle. This high applied force contributes to the safety hazard to the operator and patients or others nearby. Kulli's needle is cantilevered from the syringe holder joint and operates as a hinged joint, that is, the needle injection point actually pivots from the tip of the holder because of the clearance required between the needle ferrule groove and the holder leaves of the syringe body to accomplish needle installation and separation to/from the syringe body. Being a hinged joint, the resulting pivoting action of the needle during the penetration in the skin can result in skewed needle penetration in the skin and beyond and possibly cause injury to the patient. On the other hand, tightening up the clearance at the joint will only increase the axial force required to expel the needle and aggravate the already dangerous hazard to the user or others.

Accordingly, there is a need for an improved, simple and inexpensive needle-bearing syringe which can be operated without using high axial forces, can expel the needle simply and directly, not passively, can be safely handled after use and whose operation can be easily learned. The previously described patents require several actions, from several components, to accomplish needle removal. The various interrelated mechanical operations compound the possibility that mechanism malfunctioning will occur especially when components are plastically deformed. Similarly, the use of passive energy devices (i.e. springs, etc.) where no operator control can be exercised if needed, reduces confidence in the successful operation of the mechanism. This is complicated by the effects on clearance that the passive device must operate within to compensate for the resulting plastic component distortions and/or ruptures incorporated in the designs.

SUMMARY OF THE INVENTION

The improved syringe of the present invention satisfies the shortcomings of other prior art devices. An object of the present invention is to utilize to the greatest extent a syringe shaped similarly to those currently in use. The attachment of the hypodermic needle to the syringe would also be similar except that it would be installed from the larger open end of the syringe using the sterile packaging fixture containing the needle. After the syringe has been used, this same packaging fixture is used to remove and contain the needle. The needle would be removed by medical personnel by maintaining either hand on the syringe, inserting the fixture (depository) into the syringe with the other free hand and then rotating the depository fixture less than 90 degrees (in either direction) to directly engage and axially load the needle capsule to effect expelling and subsequent capture of the needle. The only energy needed to propel the needle into captivity makes use of the inherent elasticity of the resilient components created during the rotation of the depository when removing the needle. The syringe body may be reused after the installation of a new needle.

The present invention includes a needle capsule which has a needle for transmitting blood from a patient to a vial. The needle capsule is mounted within a syringe body. A toggle means propels the needle capsule into a depository when a predetermined amount of relative rotation is imposed between the depository and the syringe body.

Further features of the improved syringe of the present invention are set forth in the following detailed description taken in conjunction with the accompanying drawings.

FIG. 3A is a subassembly of the needle/capsule, shown on an enlarged scale, which is mounted within the syringe body of FIG. 1;

FIG. 3B shows the longitudinal view of FIG. 3A rotated 90 degrees about the axis;

FIG. 3C is an end view taken in line with the axis of FIG. 3A;

FIG. 3D is an end view taken in line with the axis of FIG. 3A;

FIG. 4A shows a longitudinal section of the syringe body;

FIG. 4B shows the longitudinal section of FIG. 4B rotated 90 degrees about the axis;

FIG. 4C is an end view taken in line with the axis of FIG. 4A;

FIG. 4D is an end view taken in line with the axis of FIG. 4A;

FIG. 4E is an enlarged partial longitudinal section of FIG. 4B;

FIGS. 4F, 4G, 4H and 4J show elevation sections of FIG. 4B;

FIG. 4K represents the developed view of diameter "D" from FIG. 4A showing the ramp configuration;

FIG. 6A is a longitudinal section of the depository tube and capture sleeve;

FIG. 6B is a longitudinal section of FIG. 6A rotated 90 degrees about the axis;

FIG. 6C is an end view taken in line with the axis of FIG. 6A;

FIG. 6D is a sectional view taken in line with the axis of FIG. 6A;

FIG. 6E is a sectional view taken in line with the axis of FIG. 6A;

FIG. 6F represents the developed view of diameter "D" from FIG. 6D showing the ramp configuration;

FIG. 7A is a longitudinal section showing the attachment of the needle/capsule to the depository ready for installation of the needle/capsule;

FIG. 7B is similar to FIG. 7A except the sequence shows the needle/capsule just before it engages with the body locking features;

FIG. 7C is an enlarged partial longitudinal section of the end of FIG. 7B;

FIG. 7D shows the final installed position of the needle/capsule into the syringe body;

FIG. 7E is an axial cross section of the depository shown in FIG. 7A taken along the line 7E–7E.

FIG. 8A is an enlarged partial longitudinal section of the depository installed into the syringe preparatory to extracting the needle/capsule;

FIG. 8B is a longitudinal section showing the captured position of the needle/capsule after it has been ejected from the syringe body into the depository;

FIG. 8C is an enlarged partial longitudinal section taken from FIG. 8B showing the capture of the needle/capsule in the depository;

FIG. 8D shows a longitudinal view of the depository, with the needle/capsule captured within, and a longitudinal section of the empty syringe body after the ejection of the needle/capsule;

FIG. 9A is a longitudinal section identifying the syringe and depository prior to needle/capsule removal;

Figure 10A:
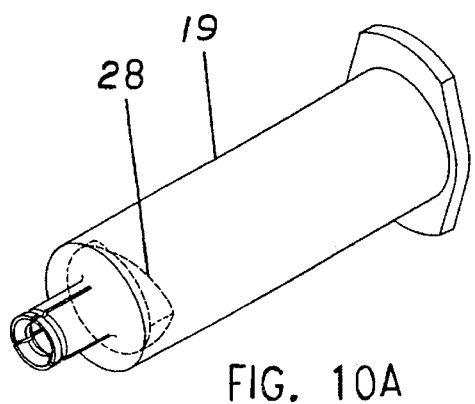
Figure 10B:
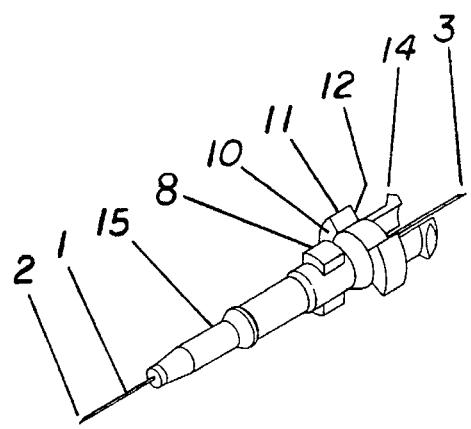
Figure 10C:
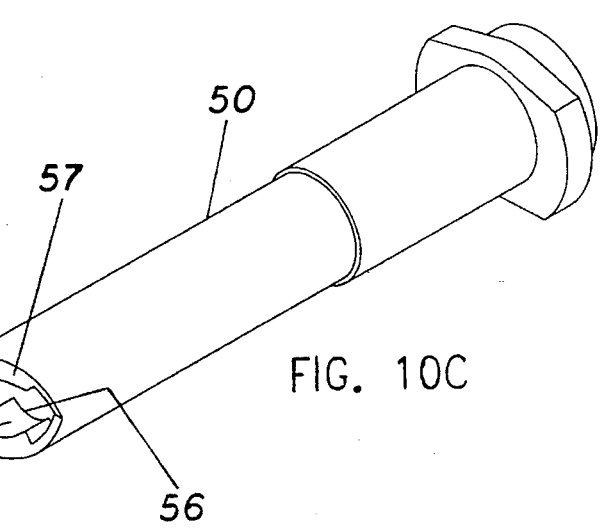
Figure 10D:
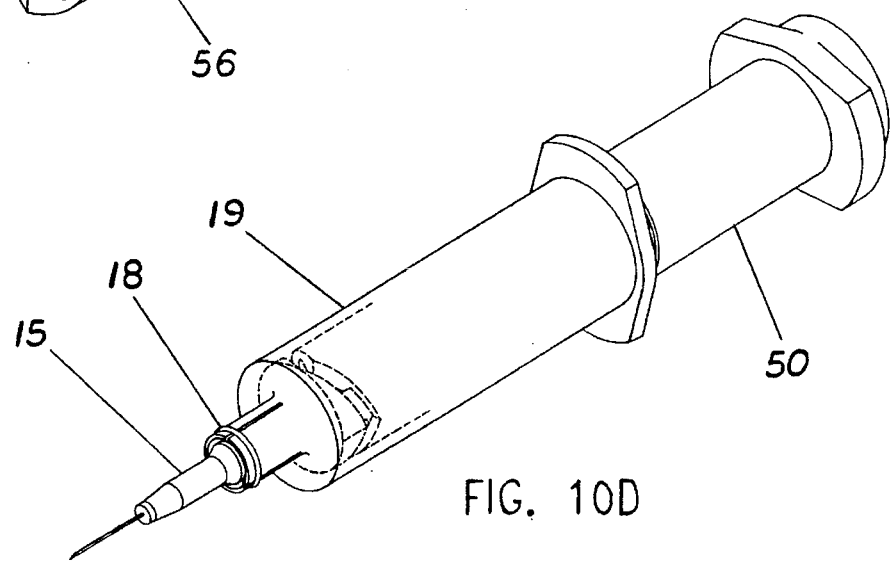

FIGS. 9B, 9C and 9D are axial cross-sections from FIG. 9A showing the orientations of the needle/capsule breech with respect to the depository breech during 1) installation, 2) after the depository is rotated 45 degrees and 3) after the depository is rotated 90 degrees;

FIGS. 9E, 9F and 9G show lateral views, in schematic form, the action of the ramps in expelling the needle/capsule relative to FIGS. 9B, 9C and 9D;

FIG. 10A is in isometric drawing of the syringe body;

FIG. 10B is an isometric drawing of the needle/capsule;

FIG. 10C is an isometric drawing of the depository;

FIG. 10D is an isometric drawing showing the assembly of the components in FIGS. 10A, 10B and 10C just prior to the depository ramps engaging the ramps of the syringe body;

FIG. 11A is an isometric drawing with a partial section showing the syringe body;

FIG. 11B is an isometric drawing with a partial section showing the syringe body and installed needle/capsule;

FIG. 11C is an isometric drawing of the depository;

FIG. 11D is an isometric drawing with a partial section showing the depository just installed with its ramp just nesting and contacting the syringe body ramp; and FIG. 11E is an isometric drawing with a partial section showing the result when the depository is rotated 90 degrees.

BRIEF DESCRIPTION OF THE PRESENT INVENTION

Figure 1:
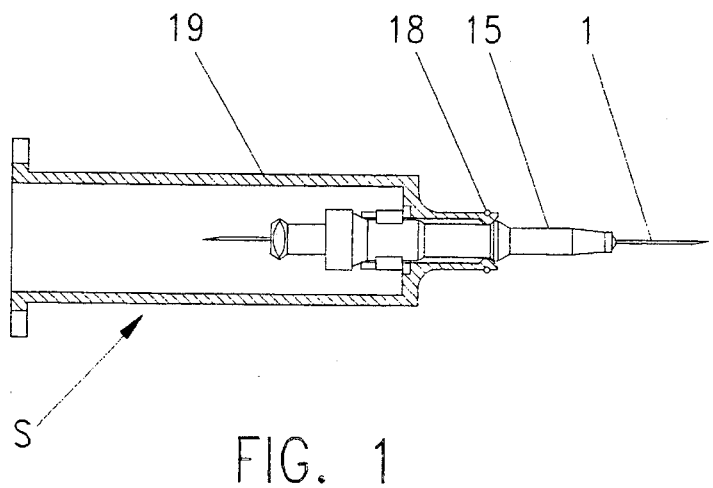
FIG. 1 is a vertical section of a syringe made in accordance with the concepts of the present invention.
Figure 2:
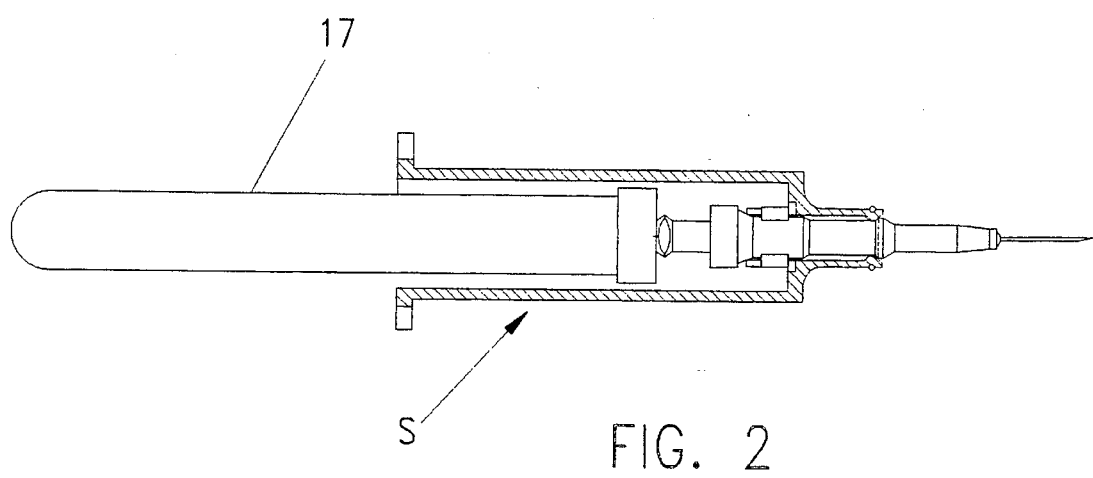
FIG. 2 shows the blood collection vial inserted into the syringe.
Figure 5:
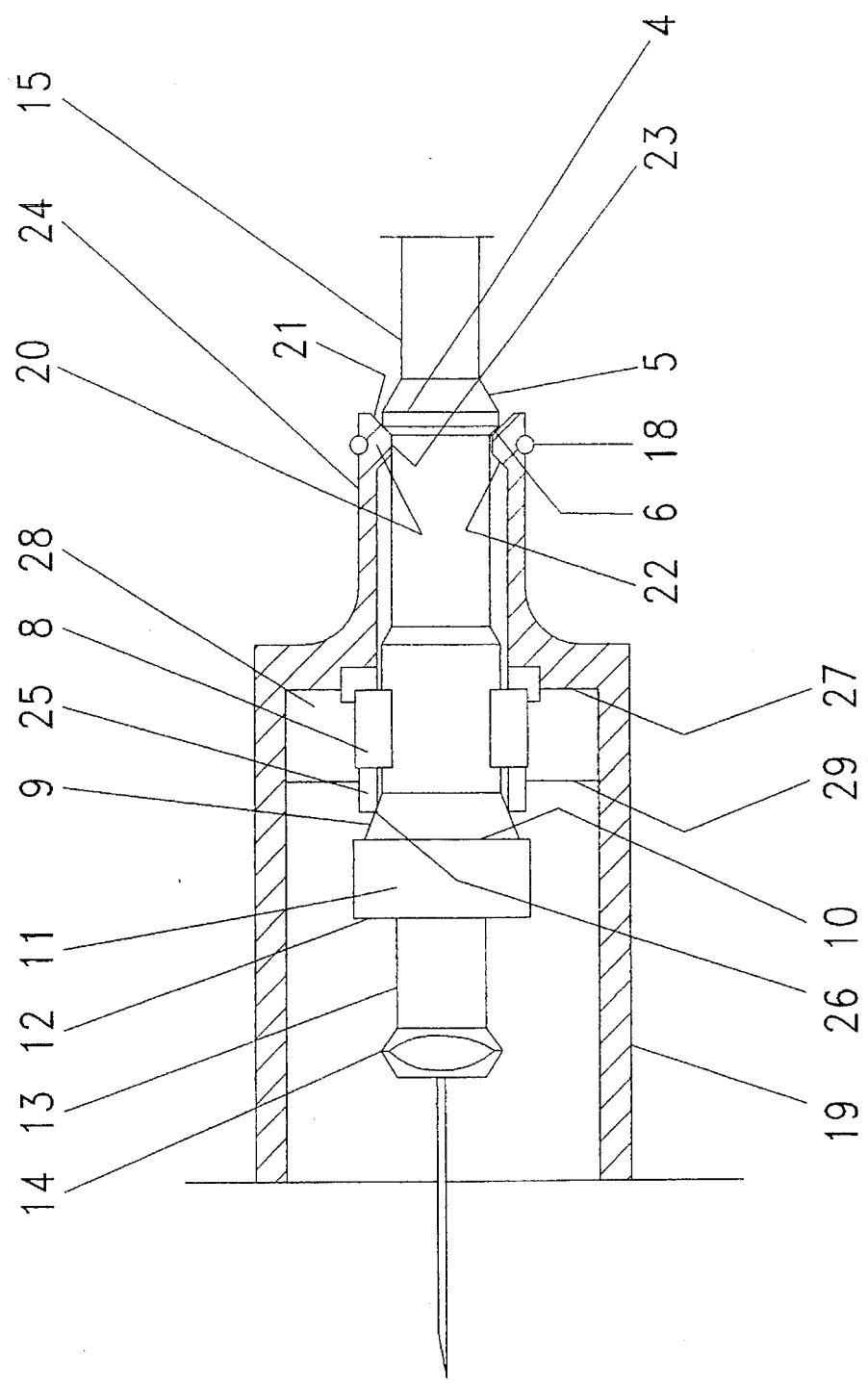
FIG. 5 is an enlarged longitudinal section of the end of the syringe body showing the interconnection with the needle/capsule subassembly.

FIGS. 1 and 11B show a safety syringe, generally designated S, with its needle 1 ready for insertion at the site of blood withdrawal. FIG. 2 shows a self-sealing blood collection vial 17 inserted into the syringe S. Blood passes through the needle 1 to fill the vial 17. To obtain additional vials of blood, the filled vial is replaced with an empty vial as is presently done by medical personnel. The general design of the safety syringe of the present invention, except as identified in this disclosure, is similar to the present state of the art and accepts present, standard sized blood sample vials 17 as shown in FIG. 2. Three general components which comprise the syringe S are shown in FIGS. 1 and 11B, and are the syringe body 19, the needle capsule assembly 15, and a split ring 18. Referring to FIGS. 3A, 3B and 10B and 11B, blood communication between the injected site and the vial 17 is accomplished by a continuous length needle 1, from the tip of the needle at 2, to the end or back of the needle at 3. The needle 1 is an integral part of the needle capsule assembly 15 and is made of stainless steel or a similar material. Support of the capsule 15 within the syringe body 19 occurs at capsule regions 4 and 9, as shown in FIGS. 3A, 3B and 5. Syringe body 19 is preferably made of plastic by means of a suitable plastic forming process, such as injection molding; however, other types of similar materials may be used.

Referring to FIGS. 4A, 4E and 5, the corresponding capsule support points for the body 19 are the internal partial diameter 26, and slope 21. A keyway 25, as shown in FIGS. 4C and 11a, positions the capsule keys 8, shown in FIGS. 10B and 11B, in proper radial orientation. As shown in FIGS. 4K, 9E, 9F, 9G and 11A, integral ramps 28 are similar to two sine waves that rise and fall between zero and 0.196 inches in 90 degree increments. These ramps 28 provide an inclined plane for raising a depository 50. The three flexible tines 24, shown in FIG. 4A, allow passage of the capsule shoulder 4 when the tines 24 are deflected radially outward approximately one-half millimeter. FIG. 5 shows an enlarged view of the tip end or portion of the body 19 and the needle capsule 15 showing how the needle capsule or capsule 15 fits and is contained within the body 19. The capsule 15 is made of molded plastic or similar material and includes a shoulder 4 that is pushed through the three flexible tines 24 of the body 19 until the capsule shoulder slope 6 passes then retracts to contact slope 21 on the body 19. This interface prevents backward motion of the capsule 15, during the needle insertion process. At the same time, excess forward motion of the needle 1 is prevented by capsule slope 9 contacting body bore partial diameter 26. The contact of the capsule shoulder slope 6 and body slope 21 and between the capsule slope 9 and body partial diameter 26, in combination with the split ring 18, maintain the capsule 15 securely within the syringe body 19 at the above mentioned two longitudinal supports. As described in detail below, split ring 18 surrounds the end of the syringe body 19 to secure and provide axial restraint for the needle capsule 15 and is preferably made of stainless steel; however other similar materials may be used.

The depository 50 is preferably made of molded plastic or a similar material and functions to install a new capsule and also to retract and contain a used capsule and is shown in FIGS. 6A–F, 10C and 11C. The depository 50 is an assembly of a depository tube 49 and a closed end cylinder 52 which captures and contains the capsule 15 after expulsion from the syringe body 19. The insertion end of the depository 50 has a breech geometry 51 which applies force to the capsule breech 11, as shown in FIGS. 10C and 11B, both to install and to withdraw the capsule 15. The contour of ramp 57 of the bottom of the depository 50, as shown in FIGS. 6F, 10C and 11C, is shaped identically to the interfacing ramp 28 contour in the syringe body 19 discussed previously. As shown in FIG. 6A, flexible struts 53 allow an extracted capsule 15 to pass through the cylinder 59 past the ends of the struts at 54. The end of the struts 54 together with the capture cap 55 effect the capture of a retracted capsule 15.

FIGS. 7A–7E portray sequentially the steps to install a capsule 15 into the syringe body 19. In FIGS. 7A and 7E the breach 51 at the end of the depository 50 slips over the back end 14 of the capsule 15 with a slight press fit. For inserting the needle 1, the breech shape 51 of the end of the depository 50 is axially aligned with the breech shape 11 of the capsule 15. Force from the depository breech 51 at surface 57 is applied to the breech end 14 of the capsule 15 at surface 12. The capsule 15 is installed in the body 19 freely until keys 8 on the capsule 15 enter the keyways 25 in the body 19, as shown in FIGS. 5 and 11B. Keys 8 and keyways 25 maintain orientation between the capsule breech 11 and the removal ramps 28 that are integral with the body 19. The purpose of the sine wave configuration, or ramps, which are used to remove the capsule 15 are discussed below. Subsequently, applying a minimal force to the capsule 15 using the depository 50, the capsule toggle shoulder slope 5, in contact with body slope 22, forces outward the three tines 24 of the body 19, which are radially squeezed inward by the split ring 18, approximately one-half millimeter thus increasing diameter 23 thereby allowing the capsule shoulder 4 to enter past the body ridge 20. Once through body diameter 23, further axial motion of the needle capsule 15 is prevented by the contact of capsule tapered region 9 against partial diameter 26 of body 19. Also, since the capsule shoulder 4 is beyond body toggle ridge 20, body diameter 23 decreases to its previous diameter. When axial force is released on the depository 50, capsule 15 retracts slightly allowing capsule slope 6 to seat against body slope 21. This is also shown in FIG. 5. At this point, the depository 50 is removed by rotating it 90 degrees to clear the breech tab 14 and pulling it out of the syringe S. The depository 50 is placed on a table for use during capsule retraction. The syringe S is now ready for injection use.

When the vial 17 is removed with the last sample of blood and placed in a rack on the table, the depository 50 will be at hand and can immediately be installed into the syringe body 19 to extract the contaminated capsule 15, as shown in FIGS. 8A–D, 9A–G, 10A–D and 11A–E. The breech end 51 of the depository 50 passes through the breech 11 clearance on the capsule 15, as shown in FIG. 9B. Since the capsule 15 is keyed to the body 19, the peaks and valleys of the ramps for the body 19 are always in proper orientation with breech 11 of the capsule 15, as shown in FIGS. 9E, 9F and 9G. As the bottom of the depository 50 goes through the breech openings of the capsule 15, the bottom 57, or ramp end of the depository 50 sockets or mates perfectly with the ramp configuration on the body 19, as shown in FIGS. 8A, 9E and 11D. At this maximum axial insertion distance for the depository 50, the elevation 56 at the top of the breech 51 of the depository is slightly below the bottom surface 10 of capsule breech 11 in FIGS. 8A and 9A.

With or without the needle 1 being in the patient, a simple twist of the depository 50 in either direction forces the depository's ramp end to ride along the syringe body's rising sine wave type ramp 28, as shown in FIG. 11A, causing the depository 50 to rise axially relative to the syringe body 19, as shown in FIGS. 11D and 11E. This action is like that of a Jackscrew device which provides axially motion of the depository 50, simulating the screw, when it is rotated against the syringe body ramp, simulating the threaded component or nut. A 90 degree rotation of the depository 50 will cause it to rise the maximum travel provided by the body ramp. As the body 19 is held by either hand, a rotation of the depository 50 causes the depository breech surface 56 to come into contact with the capsule breech surface 10, as shown in FIG. 11A and rotational sequences in FIGS. 9B–G, and loads and pulls the capsule 15 which is restrained from moving by the toggle joint, discussed below. The translation or lifting action of the depository 50, and thus the capsule 15, is restrained temporarily by the force toggle which results, among other actions, elastic stretching of the capsule 15, represented by A in FIG. 9F, elastic compression of the body tines 24, represented by B, and deflection of the capsule breeches 11, as shown in FIG. 9E. Additional rotation and the resulting higher axial load on the capsule 15 will soon overcome the resistance of the force toggle which consequently opens up and frees the needle capsule 15, represented by C in FIGS. 9F and 9G. The needle capsule 15 is expelled due its elastic energy (not unlike spring energy) from the patient and from the syringe body 19 into depository containment. The exact rotation to break the force toggle's hold on the axially loaded capsule 15 occurs between about 45 degrees and 90 degrees and is a function of the plastic material properties and component dimensions and tolerances. Positive withdrawal of the capsule 15 from the body 19 is dimensionally assured by the over-travel in the maximum 0.196 inch displacement provided by the ramps in the body 19. When the capsule 15 is propelled from the body 19, the breech lug 11 slides axially past the struts 53, deflecting them outwardly until the capsule lug 11 slides beyond the protruding strut end 54 and with an audible click, the capsule 15 strikes the end cap 55, as shown in FIG. 6A and 8B. The needle capsule 15 is captured between strut end 54 and the end cap 55. The depository 50 can then be removed from the body 19 and safely handled with the needle 1 positively contained.

The force toggle used herein is a mechanical device that will prevent premature release of a loaded joint. It is a joint that will maintain hold of one of its members until such time that the release of the member is desired. In this disclosure, it is desired that the release of the needle capsule 15 be only allowed when sufficient energy is stored within the joint members so that the needle capsule 15 can be propelled, and not just simply released. The force toggle joint includes the needle capsule 15, the tip of the syringe holder and the split ring 18. Referring to FIG. 5, leftward motion of the needle capsule 15 within syringe body 19 is resisted by slope 21 on the body 19 pushing against slope 6 on the capsule 15. Slope 21 is at the end of flexible tines 24. The flexible tines 24, without the split ring 18, can easily be deflected outward if a minimal pull force is exerted on the capsule 15. Slope 6 will simply wedge against the tines 24 at slope 21 forcing the tines 24 outward. The application of a split ring 18 surrounding the ends of the tines radially increases the deflection stiffness of the tines 24 at body region 20 which restrain motion and passage of the capsule 15 until the desired higher pull force or tension is exerted on the capsule 15. When the desired split ring stiffness is used, and when the proper tension is applied on the capsule 15 to break the force toggle, the capsule restraint is suddenly removed causing the tines 24 to deflect outward opening the passageway, and the capsule 15 propelled out of the syringe body 19 with an accompanying audible click sound. Some factors that effect the force toggle release capability discussed herein include the angles of slopes 6 and 21, the radial force of the split ring 18 and frictional coefficients of the capsule 15 and syringe body 19.

The force toggle herein is designed with the split ring 18 to provide maximum assurance of successfully expelling the needle capsule 15 especially during multiple syringe body reuse operations. The split ring 18 provides a controlled force on the body tines 24 so that expelling of the needle capsule 15 is assured considering toggle joint dimensions and tolerances, friction and local inelastic deformations. Alternate methods such as using stiffer tines or eliminating the tines 24 and split ring 18 altogether may very well provide capsule pullout restraint, however significant inelastic deformations may occur resulting in high application forces and may well jeopardize satisfactory operation of the syringe force toggle, syringe reuse capability and compromise safety.

It should be noted that during the capsule extraction process, with the medical personnel holding the flange 32 of the body shown in FIG. 4A, negligible motion of the hypodermic at the injection site will occur. More importantly, no axial motion of the hypodermic into the injected site will occur since the translation force developed to expel the hypodermic (capsule) is entirely reacted within the syringe components. The speed with which the hypodermic is extracted from the injection site will be significantly less noticeable by the patient as compared to removing it as is presently done. Thus this invention promises complete safety in withdrawing blood samples since a sharp, used, hypodermic is never exposed to cause injury or contamination to medical personnel or others. In the unlikely event components described in this invention are accidently damaged during the injection process which prevents the needle capsule 15 from being propelled into a captured state in the depository, a simple and assured fail-safe procedure is available to force a capture of the needle capsule 15. Whether the needle 1 is propelled or not, the depository 50 mechanically and positively disengages and forces the capsule 15 from the body 19 into the depository 50 without passive devices such as a spring. In this event, as determined by the lack of an audible click signifying expulsion of the capsule 15 and also observation, the assembly can be rotated and the depository 50 tapped to accelerate the capsule 15 farther into the depository capture cap.

The foregoing detailed description has been given for clearness of understanding only and no unnecessary limitations should be understood therefrom as some modifications will be obvious to those skilled in the art.

I claim:

1. A safety syringe comprising:
   a needle capsule including a needle for transmitting blood from a patient to a vial;
   a syringe body for mounting the needle capsule;
   a depository for safely receiving a used needle capsule;
   said depository and said syringe being readily rotatable in relation to each other; and
   toggle means for propelling the needle capsule into the depository upon a predetermined amount of relative rotation between the depository and the syringe, said toggle means including a split ring/shoulder lock mechanism for securing the needle capsule within the syringe.

2. The safety syringe of claim 1 wherein the toggle means includes at least one cam surface to cause translation of the needle capsule upon relative rotation of the depository and the syringe.

3. The safety syringe of claim 2 wherein said split ring/shoulder lock mechanism includes a split ring and a plurality of tines integral with said syringe body and received by said split ring.

4. The safety syringe of claim 3 wherein said plurality of tines defines a generally cylindrical area and wherein said generally cylindrical area receives said needle capsule.

5. A safety syringe for encapsulating a used hypodermic needle to prevent inadvertent injury to medical personnel or patients, comprising:
   a needle capsule assembly including a hypodermic needle for transporting blood from a patient to a removable sampling vial;
   a syringe body including a split ring/shoulder lock mechanism for securing the needle capsule within the syringe body; and
   a depository for safe receipt of said needle capsule assembly, said depository and said syringe being readily rotatable in relation to each other; and wherein said split ring/shoulder lock mechanism is releasable to propel the needle capsule assembly safely into the depository upon a predetermined amount of relative rotation between the depository and the syringe.

6. The safety syringe of claim 5 wherein said split ring/shoulder lock mechanism includes a split ring and a plurality of tines integral with said syringe body and received by said split ring.

7. The safety syringe of claim 6 wherein said plurality of tines defines a generally cylindrical area and wherein said generally cylindrical area receives said needle capsule.

* * * * *